(12) United States Patent
Hoffmann et al.

(10) Patent No.: US 7,384,503 B2
(45) Date of Patent: Jun. 10, 2008

(54) DETERMINATION OF CONTAMINANT PARTICLES IN AN AQUEOUS PULP

(75) Inventors: John David Hoffmann, Burnaby (CA); James Allen Olson, Delta (CA)

(73) Assignee: FPInnovations, Pointe Claire, Quebec (CA)

( * ) Notice: Subject to any disclaimer, the term of this patent is extended or adjusted under 35 U.S.C. 154(b) by 639 days.

(21) Appl. No.: 10/856,762

(22) Filed: Jun. 1, 2004

(65) Prior Publication Data
US 2004/0244926 A1   Dec. 9, 2004

Related U.S. Application Data

(60) Provisional application No. 60/475,475, filed on Jun. 4, 2003.

(51) Int. Cl.
*D21D 5/06* (2006.01)
*D21D 5/22* (2006.01)
*B07B 1/20* (2006.01)

(52) U.S. Cl. ............ 162/49; 162/55; 162/198; 209/17; 209/159; 209/915

(58) Field of Classification Search ............ 162/49, 162/55, 60, 198, 199, 263, 272; 209/17, 209/273, 306, 132, 155, 158, 159, 725, 915
See application file for complete search history.

(56) References Cited

U.S. PATENT DOCUMENTS

| | | | |
|---|---|---|---|
| 2,982,418 A | 5/1961 | Balley | |
| 4,222,863 A | 9/1980 | Young | |
| 4,442,003 A | 4/1984 | Holt | |
| 4,758,308 A | 7/1988 | Carr | |
| 4,993,271 A | 2/1991 | Vargason | |
| 5,087,823 A | 2/1992 | Silvy et al. | |
| 5,307,939 A | 5/1994 | Young et al. | |
| 5,518,584 A | 5/1996 | Aikawa | |
| 5,536,402 A | 7/1996 | Kluhsman | |
| 5,542,542 A | 8/1996 | Hoffmann et al. | |
| 5,624,558 A | 4/1997 | Aaltonen et al. | |
| 5,964,984 A | 10/1999 | Holmbom et al. | |
| 6,491,168 B1 | 12/2002 | Lutz et al. | |
| 6,530,481 B1 | 3/2003 | Bergdahl et al. | |

OTHER PUBLICATIONS

Gooding et al, "Paprispec: A System for Monitoring Plastic Contaminants in Pulp", TAPPI Journal vol. 80, No. 6, Jun. 1997, pp. 191-196.

(Continued)

*Primary Examiner*—Eric Hug
(74) *Attorney, Agent, or Firm*—Ogilvy Renault LLP

(57) ABSTRACT

A method and system for determining trace oversize contaminant particles in a paper-making pulp employs a screen assembly having a screen housing with a screen mounted therein, and ports for introduction of aqueous pulp and rinsing and flushing fluids, and for withdrawal of screened aqueous pulp, the screen housing has no port designated for the sole purpose of removing accumulated contaminant particles from the screen housing; instead the port employed for introduction of aqueous pulp and which may also be employed for introduction of rinsing fluid to the housing, is employed as the flushing port for removal of contaminant particles.

12 Claims, 3 Drawing Sheets

OTHER PUBLICATIONS

Friesen et al, "Pressure Screen System Simulation for Optimal Fractionation", Annual Meeting—Technical Section, Canadian Pulp and Paper Association, Preprints 2002, vol. C, 2002, pp. C33-C38.

Sithole et al, Determination and Classification of Contaminants in Recycled Pulps by Screening Techniques, Progress in Paper Recycling, Nov. 1998, vol. 8, No. 1, pp. 34-43.

Robitaille, Plastic Contamination in the Pulp Mill: An Overview:, Pulp Pap Can, Jan. 1998, vol. 89, No. 1, Jan. 1998, pp. 121-125.

DETERMINATION OF CONTAMINANT PARTICLES IN AN AQUEOUS PULP

CROSS-REFERENCE TO RELATED APPLICATIONS

This application is related to U.S. Provisional Application Ser. No. 60/475,475 filed Jun. 4, 2003 and the benefit under 35 USC 119(e) of such US Provisional application is claimed.

BACKGROUND OF THE INVENTION i) Field of the Invention

This invention relates to contaminant detection in paper pulp, and more especially to a method and device for detecting and separating oversize contaminant particles from virgin pulp and recycled pulp. The invention also relates to a method and an apparatus for separating the contaminants from pulp and isolating the oversize contaminants.

ii) Description of the Prior Art

Pressure screens are commonly used in the Pulp and Paper Industry to separate oversize contaminants from good pulp fibre.

A basic industrial pressure screen consists of a housing equipped with a pulp feed port, accept port and reject port. Within the housing, a screen cylinder, also referred to as a screen plate, is designed to allow good fibre to pass through its small apertures but at the same time prevent oversize contaminants from going through. These oversize materials remain on the feed side of the screen cylinder and work their way down its length, until they exit the screen housing through the reject port. Accepted material, material that has passed through the screen cylinder, exits the screen housing via the accept port. Usually a rotor is used to generate pressure pulsations which prevent blinding of the screen plate openings.

Below are some of the more current U.S. patents referencing such screening devices.

1) U.S. Pat. No. 5,624,558 April 1997 "Method and apparatus for screening a fibre suspension" Frank Aaltonen, Frey Frejborg 2) U.S. Pat. No. 5,255,788 October 1993 "Pressure sorter" Reimund Rienecker, Peter Schweiss & Theodor Bahr 3) U.S. Pat. No. 5,232,552 August 1993 "Screening device" N. Jorgen Lundberg, Alf I. Lindstrom 4) U.S. Pat. No. 5,186,332 February 1993 "Paper stock screening apparatus having heavy rejects trap" Derald Hatton, Joseph Constiner & David Suica Below are a number of "non-typical" screening related patents.

5) U.S. Pat. No. 5,518,584 May 1996 "Device for detecting foreign matter in pulp suspension" Yoshihiko Aikawa 6) Ca 2106211 September 1999 "Method of detecting foreign matter in pulp suspension and device for detecting the same" Yoshihiko Aikawa (same as U.S. Pat. No. 5,518,584 above)

7) U.S. Pat. No. 5,542,542 August 1996 "System for detecting contaminants" John Hoffmann, Robert Gooding, Norman Roberts & Robert Hart (Paprican is the assignee)

8) Ca 2,205,542 May 2002 "System for detecting contaminants" John Hoffmann, Robert Gooding, Norman Roberts & Robert Hart (Paprican is the assignee) (same as U.S. Pat. No. 5,542,542 above)

9) U.S. Pat. No. 4,222,863 September 1980 "Screening apparatus and method" Douglas Young 10) U.S. Pat. No. 5,407,538 April 1995 "Device for separating a mixture of paper pulp and contaminants" Jean Lamort.

A number of patented devices do not use a screening device to separate contaminants. Some patents of interest in this category include:

11) U.S. Pat. No. 4,758,308 July 1988 "System for monitoring contaminants with a detector in a paper pulp stream" Wayne Carr 12) U.S. Pat. No. 5,733,413 March 1998 "Method for removing contaminants from aqueous paper pulp" J. Alan Lawson.

SUMMARY OF THE INVENTION

It is an object of this invention to provide a method for determining contaminant particles in an aqueous paper-making pulp.

It is a further object to provide a screen assembly for use in such a method.

It is yet another object to provide a contaminant monitoring assembly for use in such a method.

In accordance with one aspect of the invention, there is provided a method for determining contaminant particles in an aqueous paper-making pulp comprising a) providing a screen assembly comprising a screen supported in a housing, said housing having first and second zones separated by said screen,
a first port in said housing communicating with said first zone, and a second port in said housing communicating with said second zone, b) feeding an aqueous paper-making pulp into said first zone through said first port, along a first flow path in said first zone and through said screen to deliver a flow of a screened aqueous suspension of pulp fibres to said second zone while retaining contaminant particles present in said aqueous pulp, in said first zone, c) withdrawing the screened suspension through said second port from said second zone, d) discontinuing steps (b) and (c), feeding a rinse fluid into said first zone to entrain residual pulp fibres in said first zone, and flush them through said screen as a flushed fibre suspension and withdrawing the flushed fibre suspension through said second port from said second zone, while retaining contaminant particles in said first zone, e) discontinuing step (d), feeding a flush fluid into said first zone to entrain contaminant particles accumulated in said first zone, and flowing said entrained particles out of said first zone through said first port, and f) recovering the contaminant particles from said dispersion.

In accordance with another aspect of the invention, there is provided a screen assembly for use in determining particles in an aqueous paper-making pulp, comprising:

i) a screen housing, ii) a screen mounted within said housing, and first and second zones in said housing defined between said housing and said screen, such that said first zone defines an upstream zone and said second zone defines a downstream zone, relative to said screen, in a contaminant separating mode of operation of said screen assembly;

iii) a first port in said housing communicating with said first zone, and a second port in said housing communicating with said second zone, said first port being a feed port for delivery of aqueous paper-making pulp into said housing during a contaminant separating mode of operation of said screen assembly, and said first port being an exit port for removal of separated contaminant particles from the housing in a contaminant sampling mode of operation of said screen assembly.

In accordance with yet another aspect of the invention, there is provided a contaminant monitoring assembly for determination of contaminant particles in an aqueous paper-making pulp comprising (a) a screen assembly of the invention; and (b) a first valve controlled flow line communicating with said first port, said first flow line having first and second valve controlled branch lines communicating therewith, said first branch line communicating with a source of aqueous pulp during the contamination separating mode of operation of the screen assembly, and said second branch line communicating with a contaminant particle collection means during the contaminant sampling mode of operation of the screen assembly.

In accordance with still another aspect of the invention, there is provided a screen assembly for screening contaminant particles from an aqueous paper-making pulp, comprising i) a screen housing,
ii) a screen mounted within the screen housing; said screen being effective to screen out contaminant particles from an aqueous paper-making pulp flowing through the screen,
iii) a first port in said housing, said first port being the sole port for feed of the aqueous pulp into the housing for flow through said screen,
iv) a second port in said housing for withdrawal of screened pulp from said housing, and
v) a third port in said housing for flow of rinse and flush fluid into said housing,
said first port being the sole port for removal of contaminant particles screened from the aqueous pulp.

LISTING OF PARTS IN DRAWINGS

1—fresh water line
2—first three way valve
3—line connecting first and second three way valve
4—line connecting second three way valve to screen housing
5—second three way valve
6—feed sample line—delivers pulp from mill to second three way valve
7—screen assembly
8—screen accept line connecting housing to two way valve
9—two way valve for screen accept line
10—screen accept line, returns clean screened pulp back to pulp mill process
11—fresh water line from two way valve to screen housing (feeding radial wash ports)
12—two way valve for fresh water line
13—fresh water line
14—line connecting first three way valve to sample cup
15—wire mesh bottomed sample cup
16—drain line for sample cup
17—fresh water line from two way valve to screen housing
18—two way valve for fresh water line
19—fresh water line
20—Trace Contaminant Monitoring System
100—screen housing
109—70 to 100 mesh wire screen attached to bottom of screen cup
110—rotor cap—close tolerance to housing provides protection for screen
111—screen retaining housing
112—rotor foil—produces pulsations that keep screen cylinder slots from plugging
113—screen rotor
114—rotor base cavity—an area for contaminants to collect
115—inclined radial venting wash ports—directed at rotor base cavity
116—screen cylinder—allows pulp fibre to pass but retains oversize contaminants
117—fresh water port
118—feed port/nozzle, tangential inlet design—accelerates pulp as it enters screen
119—screen rotor shaft
120—primary screening chamber
121—circular screen housing wall—of primary screening chamber
122—narrow annular opening—between rotor cap and screen plate retaining housing
123—screening zone—area between screen rotor and slotted screen cylinder
124—accept port—after pulp passes through the screen cylinder it enter this chamber
125—bore
200—first zone
202—flow path
204—second zone

DETAILED DESCRIPTION WITH REFERENCE TO DRAWINGS

Figure 1:
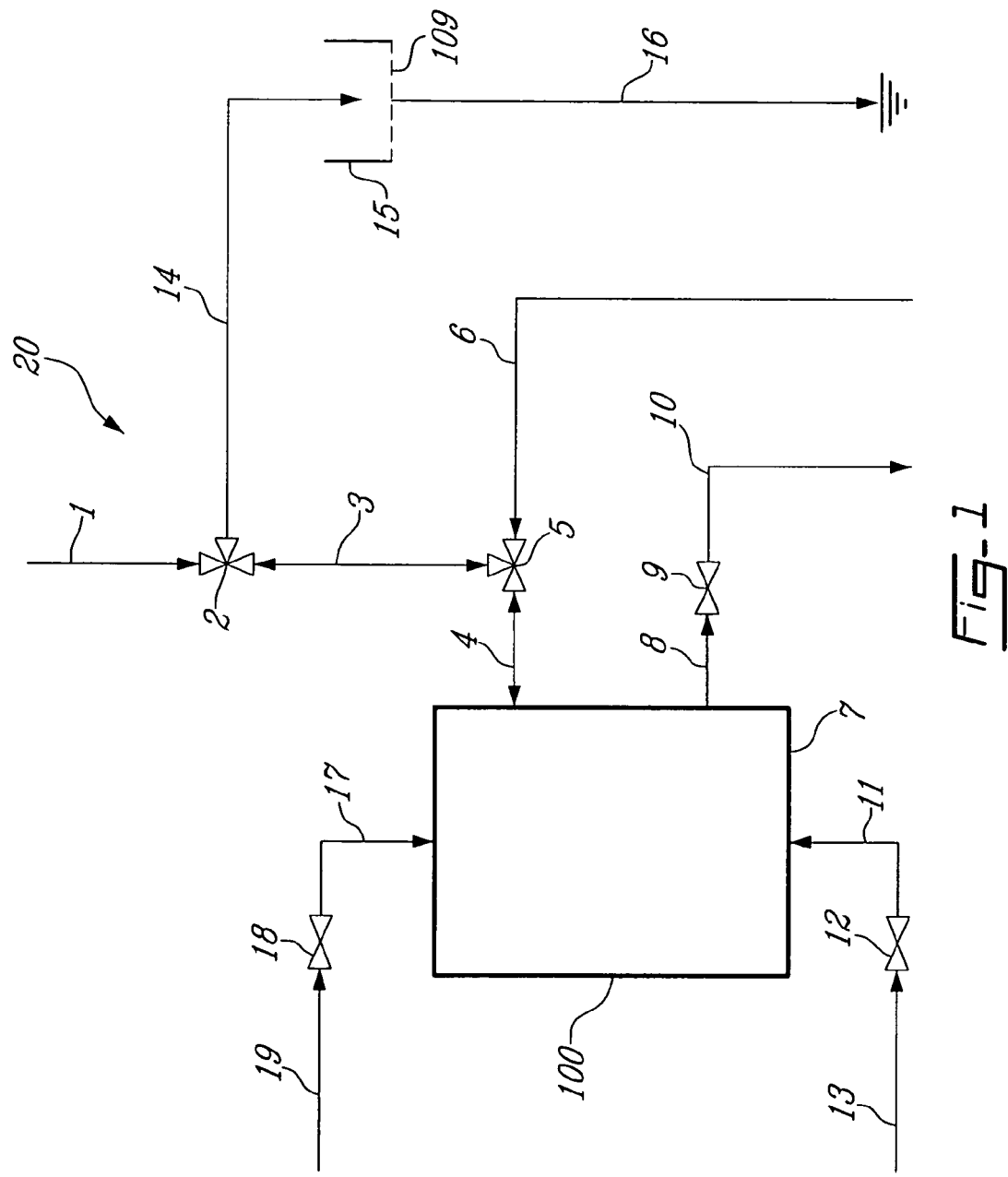
FIG. 1 illustrates schematically a Trace Contaminant Monitoring System of the invention.

With further reference to FIG. 1, a Trace Contaminant Monitoring System 20 of the invention has a screen assembly 7, a line 4 for introduction of aqueous pulp and for removal of accumulated contaminant particles from the pulp; a screen accept line 8 for withdrawal of screened pulp from screen assembly 7; fresh water lines 11 and 17 to feed rinse water to screen assembly 7 and a wire mesh bottomed sample cup 15 to collect contaminant particles removed from screen 7 via lines 4, 3 and 14. A feed sample line 6 and a connector line 3 communicate with a second three-way valve 5.

A first three-way valve 2 connects line 34 3, independently, to lines 1 and 14. Line 3 connects to first three-way valve 2 and line 14 communicates with sample cup 15.

Sample cup 15 has a wire screen 109 and a drain line 16.

The screen accept line 8 connects with a screen accept line 10 via a two-way valve 9. Screen accept line 10 returns clean screened pulp back to the pulp mill process or to another desired site.

Fresh water line 11 communicates with fresh water line 13 via two-way valve 12. Fresh water line 13 connects to a source of fresh water for rinsing and flushing during Rinse and Sample modes of operation.

A fresh water line 17 connects with fresh water 19 via two-way valve 18 for delivery of rinse and flush water during the Rinse and Samples modes of operation.

Figure 2:
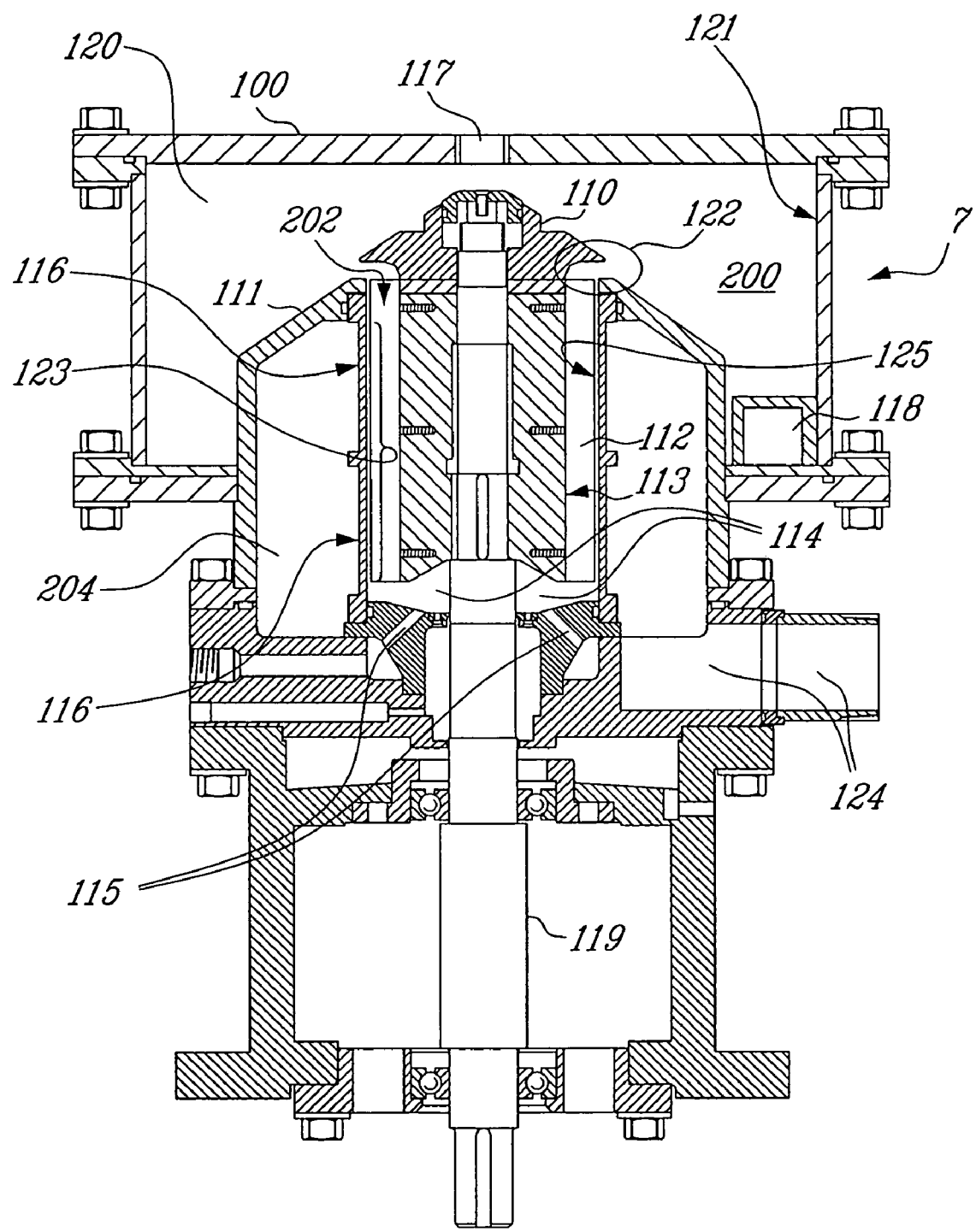
FIG. 2 is a vertical cross-section of a screen assembly for use in the system of FIG. 1.
Figure 3:
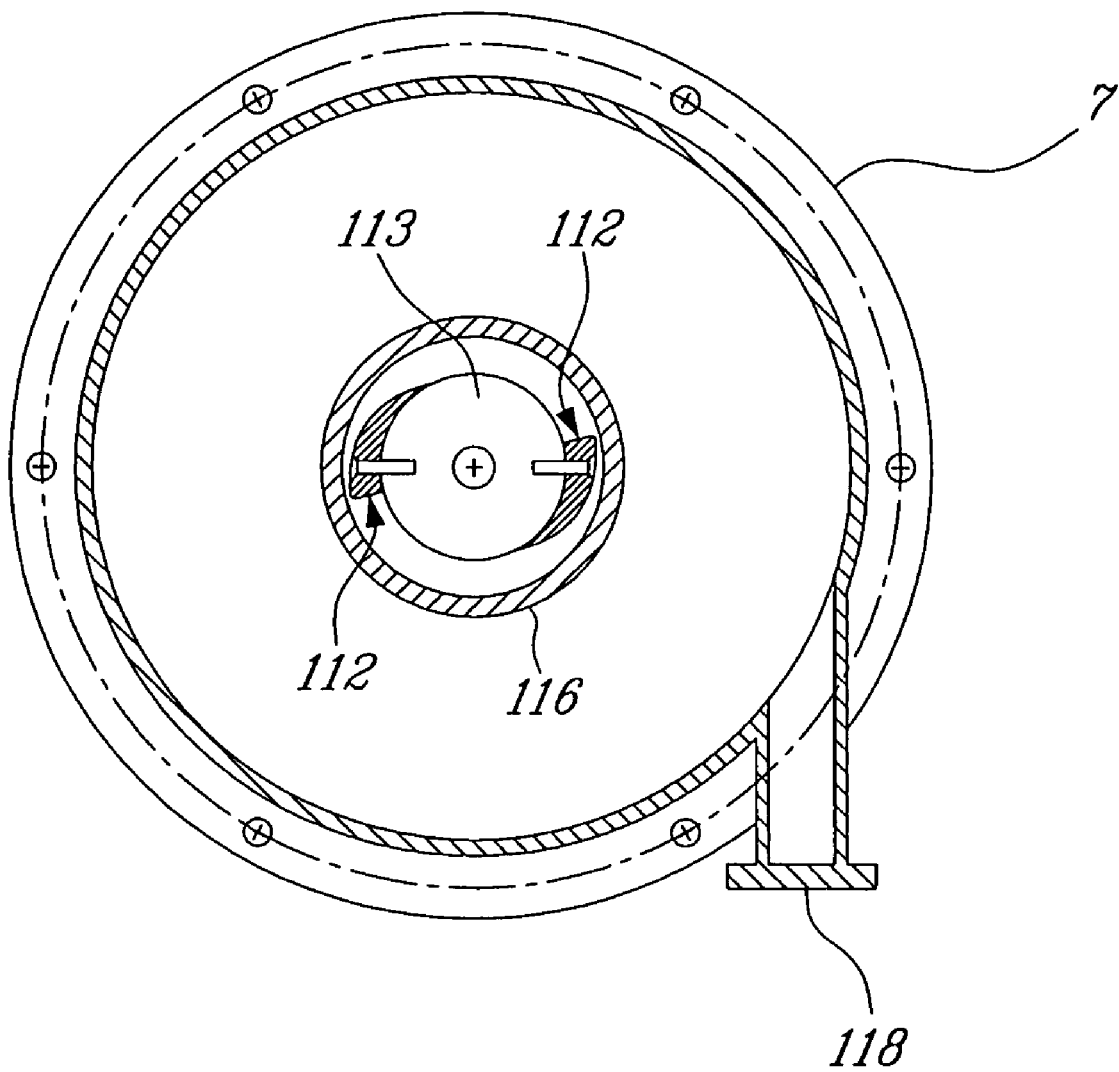
FIG. 3 is a horizontal cross-section of the screen assembly of FIG. 2.

With further reference to FIGS. 2 and 3, screen assembly 7 is shown in greater detail.

Screen assembly 7 has a screen housing 100 in which a cylindrical screen 116 is mounted in a screen retaining housing 111.

A screen rotor 113 mounted on a screen rotor shaft 119 extends centrally of bore 125 of cylindrical screen 116.

A pair of rotor foils 112 are disposed radially of screen rotor 113.

Rotor 113 has an upper rotor cap 110 which, together with retaining housing 111, defines a narrow annular opening 122 to bore 125.

In bore 125, there is defined a screening zone 123 between screen rotor 113 and cylindrical screen 116.

A rotor base cavity 114 is disposed below screen rotor 113.

The cylindrical screen 116 has openings, preferably narrow slots, which permit passage of pulp fibres but prevent passage of oversize contaminant particles. Screen assembly 7 includes a feed port 118 which communicates with line 4 of FIG. 1 and a fresh water port 117 which communicates with line 17 of FIG. 1.

Screen assembly 7 includes an accept port 124 which communicates with line 8 of FIG. 1 and inclined radial venting wash ports 115 which communicate with line 11 of FIG. 1.

Housing 100 has a primary chamber 120 which, together with screening zone 123, forms a first zone 200 of screen assembly 7. First zone 200 is essentially an upstream zone of assembly 7 relative to screen 116, during a Run or Separating mode of operation in which contaminant particles are separated and screened from aqueous pulp and a clean or screened aqueous pulp is withdrawn from screen assembly 7. The rotor base cavity 114 also forms part of first zone 200.

A flow path 202 for flow of aqueous pulp from feed port 118 through primary chamber 120 and screening zone 123 is defined within first zone 200.

A second zone 204 is defined between cylindrical screen 116 and screen retaining housing 111 and is thus downstream of screen 116 during the aforementioned Run or Separating mode of operation.

FIG. 1 thus describes the plumbing arrangement associated with screen assembly 7. The screen assembly 7 is run in three distinct modes; Run, Rinse and Sample.

In the Run mode, a sample of pulp is continually drawn from a mill's main stock pipe. This pulp is piped into the feed sample line 6, through the second three way valve 5, into line 4, which delivers the pulp into the screen assembly 7. Line 8, valve 9 and line 10 are open to allow the clean screened pulp to be returned back to the mill process. In a typical Run mode, valve 12 and valve 18 are in the closed position and no dilution/rinse water is running in lines 11, 13, 17 and 19.

In the Rinse mode, line 6 is closed by the second three way valve 5 and line 3 is opened. Line 1 is opened by the first three way valve, allowing fresh water to pass from line 1, through first valve 2, into line 3, out the second three way valve 5 and into line 4. Water then passes through line 4 and is delivered to the side of the screen assembly 7. At the same time water is also flowing in line 13 through valve 12 into line 11 and into the inclined radially venting wash ports 115 located under the screen rotor 113. Also valve 18 is partially open allowing fresh water to pass through lines 19, 17 and into the screen fresh water port 117. Line 8, valve 9 and line 10 are open to allow the rinse water containing pulp fibre washed from the screen 116, and exposed surfaces of the first zone 200 in flow path 202, to flow through screen 116 as a clean screened pulp and water and to exit through second zone 204 and accept port 124 to be returned back to the mill process.

During the Rinse mode, contaminant particles in first zone 200 are retained in the first zone 200.

The Sample mode is the final mode of operation. Here the three way valve 5 is positioned to allow the collected oversize contaminants to be flushed out of the screen assembly 7 into line 4, through valve 5, into line 3, through valve 2, into line 14 and deposited in the wire mesh bottomed collection cup 15. During the flushing process, line 8 is closed off by valve 9, valve 18 is partially open permitting flush water into line 17, through the fresh water port 117 and into the top of the screen assembly 7. Valve 12 is open allowing clean flushing water to pass through line 11 into the inclined radially venting wash ports 115 under the rotor base cavity 114. This upward flow is necessary to cleanse the screen assembly 7 of all contaminants collected.

FIG. 2 is a scaled vertical cross-sectional view of the TCMS screen assembly 7. FIG. 3 is a scaled horizontal cross-section of the primary screening chamber 120 of the TCMS screen assembly 7 with screen retaining housing 111 removed for clarity.

In the Run mode, pulp slurry enters the screen housing through feed port or nozzle 118. As the pulp passes through the feed port 118, its velocity is increased. The feed port 118 enters the primary screening chamber 120 in a tangential orientation. Tangential feed port 118 exiting into a circular housing produces a centrifugal effect that causes heavy contaminants in the feed pulp to orbit on or near the outer wall 121 of the screen housing 100. Lighter or smaller contaminants are carried to the annular opening 122 located at the base of the rotor cap 110 by the flow of pulp 118 in flow path 202. The rotor cap 110 and screen retaining housing 111 produce a very narrow annular opening 122 that allows all pulp fibre to enter but prevents large contaminants from entering the highly turbulent screening zone 123. If hard contaminants work their way into the screening zone 123, these materials will be small enough not to harm the sensitive finely slotted screen cylinder 116. As new pulp enters the screening zone 123, these contaminants will work their way down the screen cylinder 116 and be collected under the screen rotor 113, in the rotor base cavity 114.

After the pulp fibres pass the narrow annular opening 122, they are free to flow through the slotted screen cylinder 116, out the accept port 124 and back to the mill process stream through line 8 of FIG. 1. A rotor 113 equipped with two hydro foils 112 produces pressure pulsations that keep the slots of screen cylinder 116 from plugging with the pulp fibre. In the Run mode, the rotor 113 is only rotated in one direction, counter-clockwise. Fresh water ports 115 and 117 are typically off during this mode unless the consistency, solids content, of the feed pulp exceeds 1.5%, in which case one or both ports may be activated to dilute the incoming pulp.

After the Run mode or testing period is over the system 20 is switched into the Rinse mode. The testing period, or time the system is in the Run mode, is set by the pulp mill and is usually based on the level of contamination in the pulp and/or by how many contaminant samples the mill is able to process. Mill trials in accordance with the invention have had run times ranging from 0.75 to 7 hours. In general, mills may have run times as long as 12 or 24 hours. It is unlikely any mill would find it useful to extend the run time beyond 24 hours.

The Rinse mode, which follows directly after the Run mode, typically may be for 1 to 5 minutes, but usually lasts for only 1.5 minutes. In most cases this gives enough time to wash out all the residual fibre. If there is pulp fibre remaining in the final contaminant sample then the rinse time should be extended by 1 to 2 minutes or more.

The Sample mode follows directly after the Rinse mode. The Sample mode is typically for 1 to 5 minutes but usually lasts for about 2 minutes, after which the TCMS 20 is placed back in the Run mode again or shut down.

Every time a Run mode ends, a Rinse and Sample mode must follow in order to clear out the contaminants from within the System 20. This means the frequencies of the Rinse and Sample modes are directly linked to the frequency of the Run mode. The frequency of the Run mode is determined by the operator.

In the Rinse mode, pulp flow to the feed port 118 is stopped and fresh water is fed through the feed port 118, into the screen assembly 7. At the same time fresh water ports 115 and 117 are also activated. These three fresh water flows flush out any residual fibre within the screen and port cavities, and rinse it through the screen 116 and out the accept port 124. In order to ensure no fibre is caught on the rotor 113 or any part of the screen housing 100, the rotor 113 is stopped and rotated in the opposite direction, clockwise, for short periods of time.

Once the residual fibre has been washed out in the Rinse mode, the screen is switched to Sample mode. Valve 9 (see FIG. 1) is closed stopping the flow of fresh water out of the accept port 124. Wash ports 115 and 117 continue to flow fresh water into the screen housing 100. Feed port 118 remains open and the flush water from the other two ports carry all the oversized contaminants collected during the Run mode out through the feed port 118, into line 4, through valve 5, into line 3, through valve 2, into line 14 and into the collection cup 15 (see FIG. 1). Again the rotor 113 is stopped and rotated in the opposite direction, clock wise, for short periods of time, to ensure no contaminant material is caught on its surface or the screen housing 100.

After a Sample mode has been completed the contaminants collected during the last "Run" mode will be sitting in the TCMS's screen bottomed collection cup 15. The cup is taken off its base (located on the TCMS) and brought to the lab for inspection. In a typical inspection at the lab, the collection cup 15 is rinsed out onto a filter paper and placed under a microscope for inspection. During the inspection process the total number of contaminants in a given category are counted and recorded. Typical categories include: plastics, metals, aggregates, shives, fibre strings, knits etc . . . .

This inspection record allows the mill to monitor the contaminant levels in their finished products and gives them a chance to redirect off-grade production to less contaminant sensitive customers. A detected increase in contaminants also alerts the mill to potential process problems that may have otherwise gone by undetected. By using the TCMS, mills will have the added benefit of being able to easily monitor changes in contamination levels due to process modifications or improvements.

DETAILED DESCRIPTION

The TCMS (Trace Contaminant Monitoring System) is like a miniaturised industrial pressure screen but designed without a reject port. Contaminants remain in the screen until purged from the system after a thorough rinse procedure. Contaminants are transferred to a collection cup virtually free of residual fibre. This fibre free sample allows a technician to easily count and analyse the captured material.

TCMS, the system of the invention, although having some similarities in design to industrial pressure screens, performs some different functions and has special features that industrial screens do not. The following text will focus on how TCMS is different from industrial style screens.

At first glance, one of the more significant features of TCMS is that it has no reject port and associated reject piping. All industrial pressure screens need some type of reject port to remove the collected oversize material. Such a port may be opened continuously or in a periodic fashion depending on the industrial screen control strategy. TCMS is designed to collect trace contaminants like plastics, rubber, rock/sand, and metals but not to be efficient at collecting more common materials like shives. By using an aggressive rotor speed of the order of 3000 rpm+/-500 rpm, the screening zone environment is harsh enough to break down shives, so they usually do not remain in the system for any significant length of time. After several hours of screening, the small amounts of trace contaminants collected, will tend to remain below the rotor base where there is a specially designed containment cavity. After the test period is over a radial array of fresh water rinse ports located beneath the rotor base are activated to flush the contaminants out of the screen via the feed port. By not retaining much of the common contaminants like shives and by storing the collected contaminants under the rotor, the TCMS screen does not employ a reject port.

Another reason for not designing a reject port was to eliminate an area where fibre could get trapped. The TCMS operates in three distinct modes; Run, Rinse and Sample. During the Rinse mode all undersize materials, especially pulp fibres, must be completely rinsed out the screen through the accept port. Any more than a few milligrams of residual fibre will make the subsequent contaminant sample analysis very difficult. A reject port would become a site where fibre may be retained during the Rinse mode and become dislodged during the Sample mode, thereby contaminating the reject sample. It is imperative that the reject sample not be contaminated with any amount of pulp fibre.

Aside from having no reject port the TCMS screen housing was designed to minimize corners, crevices or edges where pulp could be trapped during the rinse mode and cause contamination during the sample collection mode. An arrangement of two-three way diverter style valves, allows the thorough flushing of both feed and accept ports, and associated piping, during the rinse mode. This prepares the valves and piping for transferring of the contaminant sample from the screen to a collection cup without adding any amount of residual pulp fibre.

Industrial screens are typically used for the removal of contaminants from pulp. They are not designed to present these contaminants, free of fibre, to a collection cup. Producing a contaminant sample virtually fibre free is a most important feature of TCMS. It only takes a few milligrams of residual fibre to cause significant difficulties in subsequent contaminant analysis steps. None of the prior patents identified herein describe this distinct feature.

Not only does the rotor have a built in contaminant storage area, but the top of the rotor, the rotor cap, protects the delicate screen cylinder from damage. The base of the rotor cap and the top of the screen cylinder retaining housing form a narrow annular opening that pulp fibre must pass through to access the screen cylinder. In essence, this annular opening acts like a coarse pre-screening step, which prevents hard oversized contaminants from abrading or distorting the delicate slots in the screen cylinder and the foils mounted on the sides of the rotor.

The rotor is operated in both the forward and reverse directions during two of the three operating modes. In the rinse mode the rotor is operated in both directions to help dislodge any fibre that may be caught on the rotor or screen. In the sample mode it helps ensure all contaminants are flushed out from beneath the rotor and carried out of the screening zone. In the run mode the rotor must only be operated in the "forward" direction or the screen will plug or blind very quickly.

Aside from industrial screens, there exists another class of smaller screening apparatus termed "laboratory screens". Three of the most popular of theses screens include the Valley Flat Screen, Somerville Fractionator and the Pulmac Master Screen. These screens are designed to work with a small mass of pulp, typically 10 to 100 grams, and screen the sample down to contaminants only. A significant difference between TCMS and these screens is the mass of pulp they can process. TCMS can sample a mills pulp production online, up to five tonnes per day. The lab screens, on the other hand, are run in a batch mode, not on line, and are not practical for processing large masses of pulp.

For example, to screen a tonne of bleached Kraft pulp through a 0.006" slotted Valley Flat Screen at a typical rate of approximately 25 grams OD pulp/5.0 min. and based on a 6 hour actual work day, would take a little over 1.5 years to complete. Similarly, Pulmac's new high mass throughput "Master-screen" would take 278 days to complete this task. On the other hand, a tonne of pulp fed through the TCMS at 1.0% consistency would take only 8.3 hours to complete, and about half that time if the consistency is increased to 2.0%.

Mechanically the Valley Flat Screen and the Somerville Fractionator are quite different from TCMS. The Pulmac Master-screen, though closer in design to TCMS, is still significantly different. The Master-screen has a reject port, a flat non-cylindrical screen plate, low pulse rotor, runs in batch mode and is limited to about a 100 gram sample per run.

The Trace Contaminant Monitoring System or T.C.M.S. is thus a device designed to collect contaminants that are considered troublesome in the paper making, coating and printing processes. Contaminants like metal fragments, aggregates (small pebbles or rock fragments), and heavy and light weight plastics. Usually these materials exist at very low concentration levels, in the order of parts per billion, and thus are commonly called trace contaminants. To measure or quantify the concentration of these trace contaminants, it is necessary to screen many hundred kilograms of pulp. Aside from the TCMS, there is currently no practical way to screen a large enough pulp sample to collect these trace contaminants with any statistical relevance.

The system employs a ruggedly built mini pressure screen fitted with a small finely slotted screen cylinder. The TCMS is designed to continually sample a mills pulp production, in slush form, and pass it through the mini pressure screen for contaminant separation. The materials that are unable to pass through the narrow slotted apertures remain in or on the screen, until the end of the test period. When the test is over, fresh water is used first to wash any residual fibre from the screen and subsequently to flush contaminant particles to the sample cup. No other industrial or lab scale device can screen as much pulp while, at the same time, be able to provide a contaminant sample virtually free of fibre.

The list below summarizes key features that make TCMS unique:

1) No reject port—the feed port performs both duties that were previously handled by two separate ports; a feed and reject port.
2) Screen system operates in three distinct modes; Run, Rinse and Sample modes
3) Contaminant sample is virtually free of pulp fibre—due to a rigorous rinse mode.
4) Contaminants are deposited into a sample cup
5) Screen system is designed with a radial array of fresh water ports underneath the rotor base.
6) Rotor is designed with a cavity in the base to help contain and store contaminants.
7) Rotor is operated in both the forward and reverse directions during the Rinse and Sample modes.
8) The rotor cap and housing produce a narrow annular opening that all pulp must pass through before entering the screening zone. This protects the delicate screen plate located in the screening zone from abrasion and damage due to hard oversized contaminants.

The invention is concerned with determining oversize contaminant particles.

The term "oversize" refers to a comparison of any contaminant particle's minimum dimension to the width of the apertures in the screen cylinder. A particle that is said to be oversized can not fit through any of the screen apertures no matter how the particle is orientated. Therefore the screen cylinder retains oversize contaminants but allows undersize contaminants and other undersize materials like pulp fibers to pass through the cylinder. All oversize materials are contaminants but undersize materials can be contaminants or they can be desirable materials like fibers.

Typical pulp fibres have a minimum thickness range of 0.01 mm to 0.065 mm. The slot aperture widths of the screen cylinders in the TCMS will typically range from 0.1 mm to 0.25 mm. These measurements indicate that no matter what type of wood fiber is screened and what screen cylinder slot aperture is chosen, fibre will always be able to pass through the screen plate.

The size of contaminant particles found in a pulp will range from mill to mill.

Contaminant particles that cannot pass the narrow annular opening 122 must have all dimensions greater than the distance between the rotor cap 110 and the screen retaining housing 111. In the event that a higher pulp flow rate through the TCMS is required, the annular opening distance could be increased. Conversely, if a lower flow rate is required or a higher level of screen protection is needed then the annular opening distance could be reduced.

Particles that pass the annular opening 122 but are retained by the screen cylinder 116 must have one or more dimensions within a size range greater than 0.15 mm and less than the annular opening dimension. This range is based on a screen cylinder with 0.15 mm slot aperture, in the TCMS.

Particles like fibers, or contaminant particles with at least one dimension smaller than 0.15 mm, will pass through the screen cylinder and be returned back to the mill process.

The invention claimed is:

1. A method for determining contaminant particles in an aqueous paper-making pulp comprising
   a) providing a screen assembly comprising a screen supported in a housing, said housing having first and second zones separated by said screen,
   a first port in said housing communicating with said first zone, and a second port in said housing communicating with said second zone,
   b) feeding an aqueous paper-making pulp containing contaminant particles tangentially into said first zone through said first port, thereby producing a separation of heavy contaminants from lightweight contaminants in said first zone, feeding pulp fibres and lightweight contaminants along a first flow path adjacent said screen in said first zone, and feeding the pulp fibres through said screen to deliver a flow of a screened aqueous suspension of pulp fibres from said first zone to said second zone while retaining the heavy and lightweight contaminants present in said aqueous pulp, in said first zone,
   c) withdrawing the screened suspension through said second port from said second zone,
   d) discontinuing steps (b) and (c), feeding a rinse fluid into said first zone to entrain residual pulp fibres in said first zone, and flush them through said screen as a flushed fibre suspension and withdrawing the flushed fibre suspension through said second port from said second zone, while retaining said heavy and lightweight contaminants accumulated in said first zone,
   e) discontinuing step (d), feeding a flush fluid into said first zone to entrain contaminant particles accumulated in said first zone, and flowing said entrained particles out of said first zone through said first port, and
   f) recovering the contaminant particles from said flush fluid.

2. A method according to claim 1 including a step
   g) evaluating the recovered contaminant particles as a determination of contaminant particles in said aqueous paper-making pulp.

3. A method according to claim 2 wherein said aqueous paper-making pulp in step (b) is a continuous sample flow withdrawn online from a pulp flow in pulp or paper-making, and including issuing an instruction as to said pulp flow or paper-making in response to said evaluating in (e).

4. A method according to claim 1 wherein said steps (b) and (c) are carried out on a continuous basis with a continuous flow of said aqueous paper-making pulp into said first zone and a continuous flow of screened suspension out of said second zone for a period of 0.75 to 24 hours, whereafter steps (d) and (e) are carried out sequentially for a period of less than 5 minutes each.

5. A method according to claim 1 wherein said housing is cylindrical.

6. A method according to claim 5 wherein said screen is a cylindrical screen and said second zone is disposed outwardly of the cylindrical screen, said cylindrical screen having a bore forming part of said first flow path, and subjecting said aqueous pulp in said bore to pressure pulsations effective to prevent pulp fibres from plugging said screen.

7. A method according to claim 6 wherein said bore of said cylindrical screen has a narrow annular entry opening for said pulp in said first flow path which prevents entry into said bore of large contaminant particles in said pulp, while permitting passage of pulp fibres and small contaminant particles.

8. A method according to claim 1 wherein the feeding of rinse fluid in step (d) includes a radial feed of the rinse fluid into a base lower region of said bore and a feed through said first outlet, in said first zone.

9. A method according to claim 3 wherein said steps (b) and (c) are carried out on a continuous basis with a continuous flow of said aqueous paper-making pulp into said first zone and a continuous flow of screened suspension out of said second zone for a period of 0.75 to 24 hours, whereafter steps (d) and (e) are carried out sequentially for a period of less than 5 minutes each.

10. A method according to claim 9 wherein said housing is cylindrical.

11. A method according to claim 10 wherein said screen is a cylindrical screen and said second zone is disposed outwardly of the cylindrical screen, said cylindrical screen having a bore forming part of said first flow path, and subjecting said aqueous pulp in said bore to pressure pulsations effective to prevent pulp fibres from plugging said screen.

12. A method according to claim 11 wherein said bore of said cylindrical screen has a narrow annular entry opening for said pulp in said first flow path which prevents entry into said bore of large contaminant particles in said pulp, while permitting passage of pulp fibres and small contaminant particles.

* * * * *